(12) United States Patent
Tcholakian

(10) Patent No.: US 9,566,380 B1
(45) Date of Patent: Feb. 14, 2017

(54) REUSABLE AND INEXPENSIVE CONTAINER ASSEMBLY DESIGNED FOR STORAGE OF INSULIN AMPULES AND OTHER HYPODERMIC SOLUTIONS AND PHARMACEUTICAL MEDICATIONS

(71) Applicant: Robert K. Tcholakian, West University Place, TX (US)

(72) Inventor: Robert K. Tcholakian, West University Place, TX (US)

( * ) Notice: Subject to any disclaimer, the term of this patent is extended or adjusted under 35 U.S.C. 154(b) by 0 days.

(21) Appl. No.: 14/464,716

(22) Filed: Aug. 21, 2014

(51) Int. Cl.
*A61M 5/00* (2006.01)
*A61J 1/16* (2006.01)

(52) U.S. Cl.
CPC .............. *A61M 5/002* (2013.01); *A61J 1/16* (2013.01)

(58) Field of Classification Search
CPC ............ B65D 77/0493; B65D 81/3205; B65D 81/268; B65D 81/07; G21F 5/00; A61J 1/16
USPC ....... 206/528, 592, 589, 366, 234, 379, 540, 206/446; 215/377; 220/23.89
See application file for complete search history.

(56) References Cited

U.S. PATENT DOCUMENTS

| | | | | |
|---|---|---|---|---|
| 2,915,640 | A * | 12/1959 | Grubel et al. | 250/507.1 |
| 3,275,180 | A * | 9/1966 | Optner et al. | 206/521 |
| 3,527,405 | A * | 9/1970 | Harding | A61L 9/12 206/591 |
| 3,907,145 | A * | 9/1975 | Horvath | 215/206 |
| 4,040,549 | A * | 8/1977 | Sadler | 224/483 |
| 4,133,445 | A * | 1/1979 | Mandelbaum | 220/23.4 |
| 4,805,789 | A * | 2/1989 | Lancesseur et al. | 215/6 |
| 8,087,528 | B1 * | 1/2012 | Scarlett et al. | 220/23.89 |
| 8,763,797 | B2 * | 7/2014 | Guillon et al. | 206/204 |
| 2014/0311934 | A1 * | 10/2014 | Beadles | 206/446 |

* cited by examiner

*Primary Examiner* — Chun Cheung
(74) *Attorney, Agent, or Firm* — Karen B. Tripp

(57) ABSTRACT

A description of a bottle container assembly for use by patients for daily handling of glass insulin ampules and/or a variety of prescription medications and small medicine bottles. The container assembly is designed for frequent daily use at home, work or travel. It is constructed to address the safe handling, use and safe storage of medicines and in particular the storage of a variety of glass ampules containing insulin or other hypodermic solutions. The invention provides a safe, suitable and reusable container assembly to hold various insulin ampules replacing the fragile cardboard boxes they are shipped in by the manufacturers.

12 Claims, 4 Drawing Sheets

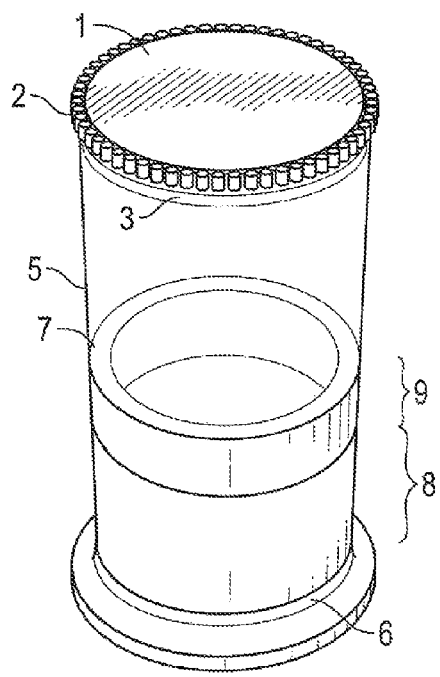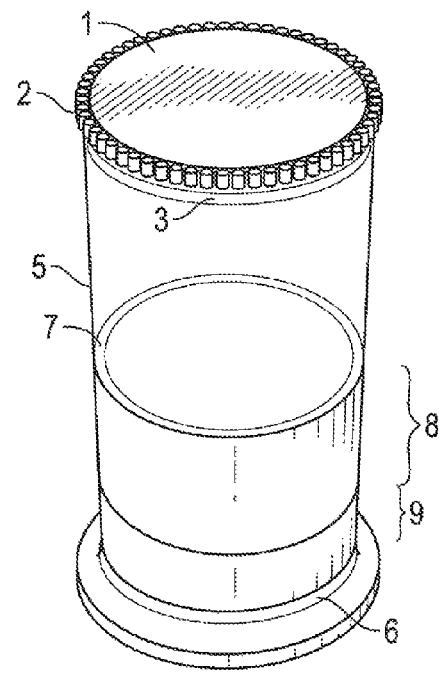
FIG. 5  FIG. 6
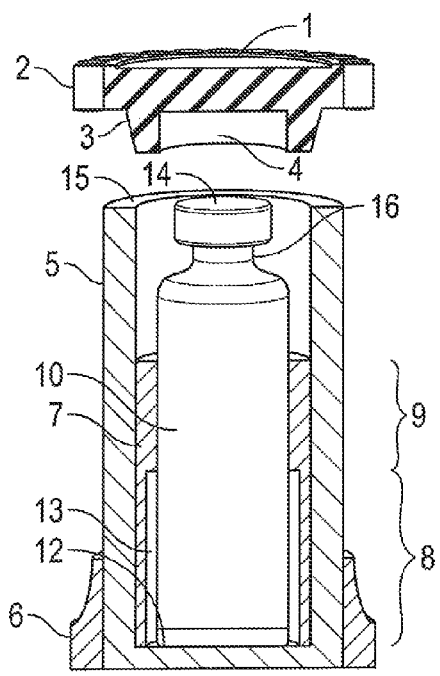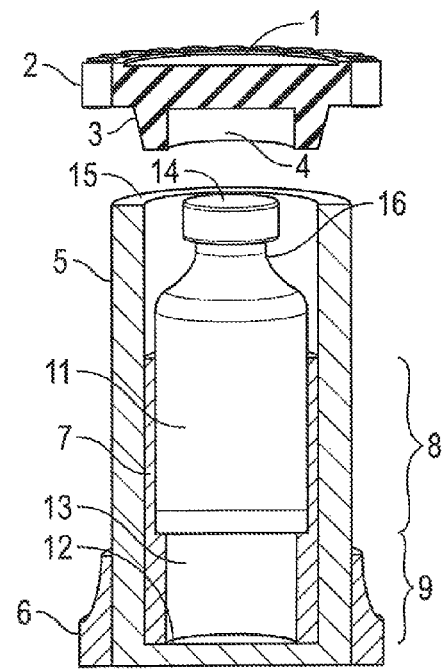
FIG. 7  FIG. 8

REUSABLE AND INEXPENSIVE CONTAINER ASSEMBLY DESIGNED FOR STORAGE OF INSULIN AMPULES AND OTHER HYPODERMIC SOLUTIONS AND PHARMACEUTICAL MEDICATIONS

FIELD OF INVENTION

The present invention relates to the field of containers. A general application of the invention concerns pharmaceutical products and in particular glass insulin ampules. The container also addresses the patients' frequent daily safe handling and transporting insulin ampules and safeguarding them and other pharmaceutical products from contamination and breakage.

BACKGROUND

Based on 2010 data published by the CDC (2011) [Centers for Disease Control and Prevention (CDC) National Diabetes Fact Sheet: 2011: "National estimates and general information on diabetes and prediabetes in the United States", Atlanta, Ga. USA.] (Reference 1). Diabetes affects 25.8 million people or 8.3% of the United States population. 18.8 million are diagnosed diabetics and 7.0 million people are undiagnosed. Applying the percentages of diabetics in the United States derived from various large population studies, it is estimated that 79 million American adults 20 years old and older are pre-diabetics.

Of the diabetic population in the US 12% use only insulin to regulate their blood sugar levels and 14% use a combination of insulin and oral medication (Reference 1). In essence, 26% of the diabetic population of 18.8 million will use a select variety and combination of injectable insulin supplied in glass ampules containing 10 cc. preparations namely: Lantus®; Novolog®; Humalog®; Novolin®; and Humulin® to mention a few. Each of these preparations is shipped or sold to the patient in a very small weak thin cardboard box. The potential for the box to fall apart, become contaminated due to multiple daily use and storage and for the glass ampule to fall and break is very real. Each broken or contaminated ampule represents a loss of $150.00 or more The invention helps not only US diabetics that are on insulin but also the hundreds of millions around the world who face certain contamination, infection and breakage from daily withdrawal and injection of insulin. The inventor personally used the device to store the two different insulin preparations he uses to medicate himself without any incident of contamination, infection or breakage of any insulin ampule over a reasonable test period.

There are a variety of containers on the market suited for pharmaceutical prescription medicines. Moreover, the expanded use of insulin for treatment of diabetes is currently more prevalent than in the past due to the production of more pure insulin preparations. Insulin can be administered by insulin pumps, insulin pens and most economically by mechanical withdrawal of hypodermic insulin solution from glass ampules. The current supply of 10 cc. of insulin solution in ampules is the least expensive of the various preparations. The glass ampules are supplied in small cardboard boxes that provide inadequate protection to the medication once the box is opened for use. There is often a deterioration of the original cardboard box due to multiple daily handling for insulin withdrawal. Furthermore, handling of the insulin containing ampule frequently increases the chance of breakage and loss of the insulin content. Also the multiple daily handling would increase the likelihood of contaminating the outside of the ampule and the hypodermic injection site leading to painful infections at such sites. The insulin preparations supplied in ampules can be kept at room temperature for up to 30 days, but the product is not marketed in a container that can safely last through such a prolonged use.

Various attempts have been made to address the containment and transport of pharmaceuticals and in particular insulin ampules. Zou Yuanyi, et al. [Zou Yuanyi, et al.; Univ Shanghai Electric Power: "portable insulin heat-preserving container with refrigerating function". Shanghai University of Electric Power, CN202687120 (U)-2013-01-23 (September 2013).] (Reference 2) relates to the complicated transport of insulin in a container that is heat-preserving and with refrigerated function. A similar approach for a diabetic traveling case is taught in [Emil G. Ehman: "Diabetic traveling case". Publication Number: U.S. Pat. No. 4,429,793A and Published as DE3316361A1, DE8313241U1 (May 1982).] (Reference 3) with use of a refrigerant to keep the insulin from spoiling. A diabetic two-fold medical case [Edna Ford: "Diabetic two-fold medical case". U.S. Pat. No. 8,550,251B1 (October 2013).] (Reference 4) is documented but the problem with these devices is that they are large, heavy and cumbersome for multiple daily use for the average diabetic patient to appreciate. They also do not address the breakage and contamination of the ampule by direct handling.

A similar large and cumbersome container as reported by Edna Ford (Reference 4) was declared by Kahilainen [Hannu Kahilainen: "Patient's container of medical equipment for use at home", [FI/FI] Ritakuja 6, Kangasala (FI). International Publication Number WO1995009579A1 (April 1995).] (Reference 5) as an invention of a container of medical equipment for use by diabetic patients. The patient's main concern is to safeguard the insulin ampule from contamination and prevent infection and breakage throughout the multiple uses per day for an average of thirty day life span of each ampule.

Other declarations dealing with the art include Koslovskyh [H Koslovsky: "Medicant withdrawal unit". U.S. Pat. No. 3,762,673 (A). (February 1973).] (Reference 6) who relates to a medical unit for withdrawing insulin with one hand, while Fuerther Guenter [Fuerther Guenter: "Diabetic set". U.S. Pat. No. 4,446,970 (A) (August 1984).] (Reference 7) presents a diabetic set with accessories for the "hygienic" withdrawal and injection of insulin. Xiaofeng Zhang, et al. [Xiaofeng Zhang, et al.: "Insulin storage containers". CN201990069 (U) (September 2011).] (Reference 8) describe an insulin storage container composed of a box and box cover with magnets and iron plates to seal and facilitate access to the insulin. Jentis Rebbecca et al. [Jentis, et al.: "Improvements in insulin preserving travel kit for diabetics". GB1017324 (A) (January 1966).] (Reference 9) and Steffen Lay, et al. [Lay, et al.: "A medical apparatus for use by a patient for medical self treatment of diabetes". WO1999059657A1 (November 1999).] (Reference 10) reported on a complicated portable container for carrying insulin during travel.

All the pertinent cited literature demonstrated costly and cumbersome devices suited for handling earlier insulin preparations when insulin was extracted from animal pancreatic tissues. The modern day insulin preparations are pure and prepared from genetically engineered cultures. Such new preparations can remain at room temperatures for up to 30 days of use.

SUMMARY OF THE INVENTION

The field of invention presents a multifunctional device that not only protects the ampule but significantly reduces, even eliminates, handling of the ampule since it would be snugly positioned inside the container assembly.

The compactness and simplicity of the container assembly will result in providing a low cost container that can be carried and transported in a variety of ways. It can be washed, disinfected with alcohol and reused over again. While in use, the device is so versatile that it can be placed on a table, desk, shelf, in a shirt pocket or in a refrigerator. It is also provided with an anti-toppler ring (6) as illustrated in FIG. 1, to prevent the container assembly from toppling and rolling to the floor. While traveling, the container assembly can be kept in a purse, in a luggage bag, in an ice chest or in a jacket pocket. Moreover, the container can be produced in a range of colors from clear acrylic to various colors of the rainbow. These are but a few of the numerous manufacturing possibilities.

In one embodiment, the present invention comprises a cylindrical container (5) with a versatile insert device (7) as illustrated in FIG. 2, to accommodate a variety of insulin ampules. A joined double cylindrical container (5) of the above forms a usable storage space for the insulin ampule for daily and travel use as illustrated in FIG. 9.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

KEY

Figure 1:
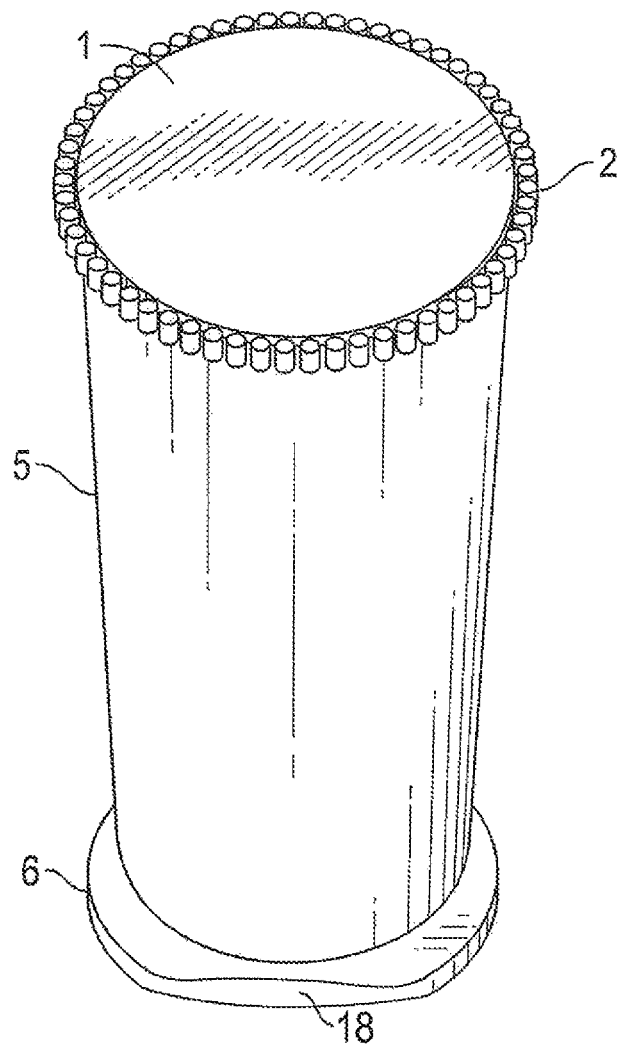

1) Cap
2) Nibs on cap edge
3) Tapered cap liner
4) Domed empty space ¼" inside cap liner
5) Cylindrical container body
6) Anti-toppler ring
7) Insert device
8) Wide thin-walled opening of insert device
9) Narrow thick-walled opening of insert device
10) Lantus® insulin ampule
11) Novolog®/Humalog®/or Humulin® ampules
12) Container flat bottom
13) Empty space inside assembled container
14) Top surface of insulin ampule
15) Top surface of open container
16) Neck of insulin ampule
17) Bridge joining two cylindrical containers
18) Notched anti-toppler ring

FIGURES

FIG. 1 illustrates the fully assembled single cylindrical container unit of one embodiment of the invention.

Figure 2:
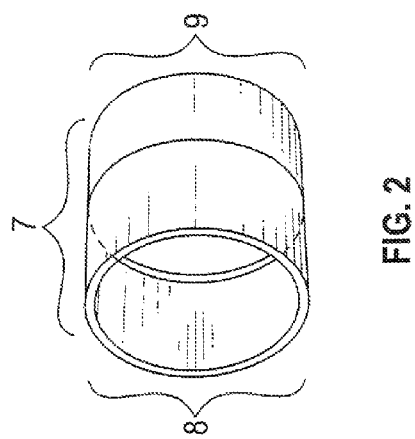

FIG. 2 illustrates the insert device (7) that slips into the cylindrical container (5).

Figure 3:
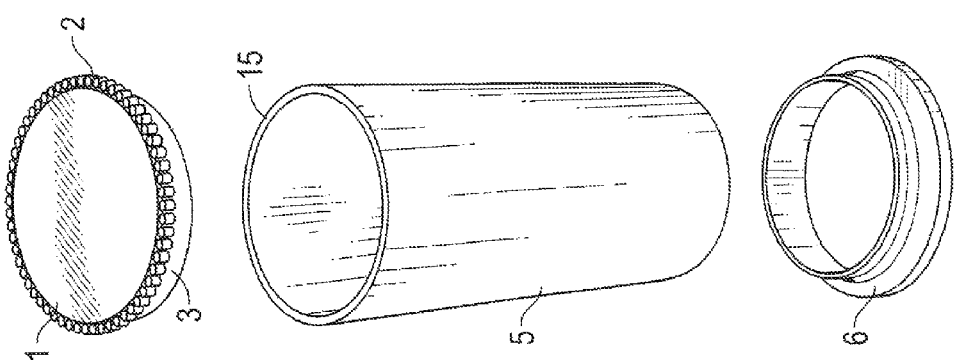

FIG. 3 illustrates an exploded view of what happens when the thin-walled end (8) of the insert device (7) is slipped into the cylindrical container (5).

Figure 4:
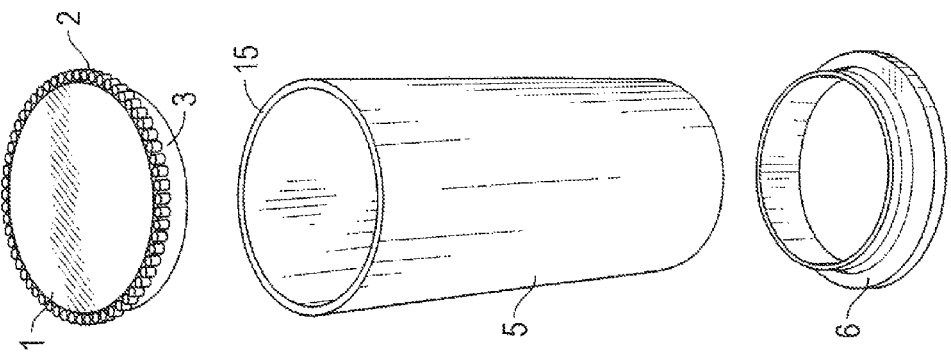

FIG. 4 illustrates an exploded view of what happens when the thick-walled end (9) of the insert device (7) is slipped into the cylindrical container (5).

FIG. 5 illustrates the position of the insert device (7) inside the cylindrical container (5) when the thin-walled end (8) is slipped into the cylinder first, exposing the thick-walled end of the insert device (9) to snuggly hold the taller Lantus® ampule (1) in a fixed position. Lantus® is a registered trademark of Sanofi Aventis U.S. LLC, A Sanofi Company, Italy.

FIG. 6 illustrates the position of the insert device (7) inside the cylindrical container (5) when the thick-walled end (9) is slipped into the cylindrical container (5) first, exposing the thin-walled end of the insert device (8) to snuggly hold the shorter Novolog®, Humalog® or Humulin® insulin ampules (11). Novolog® is a registered trademark of Novo Nordisk, Inc., Princeton, N.J. Humalog® is a registered trademark of Lilly USA, LLC, Indianapolis, Ind. Humulin® is a registered trademark of Eli Lilly and Company, Indianapolis, Ind.

FIG. 7 illustrates the position of the Lantus® ampule (10) snuggly held by the thick-walled (9) portion of the insert device (7). It also illustrates the domed empty space inside the cap liner (4).

Figure 9:
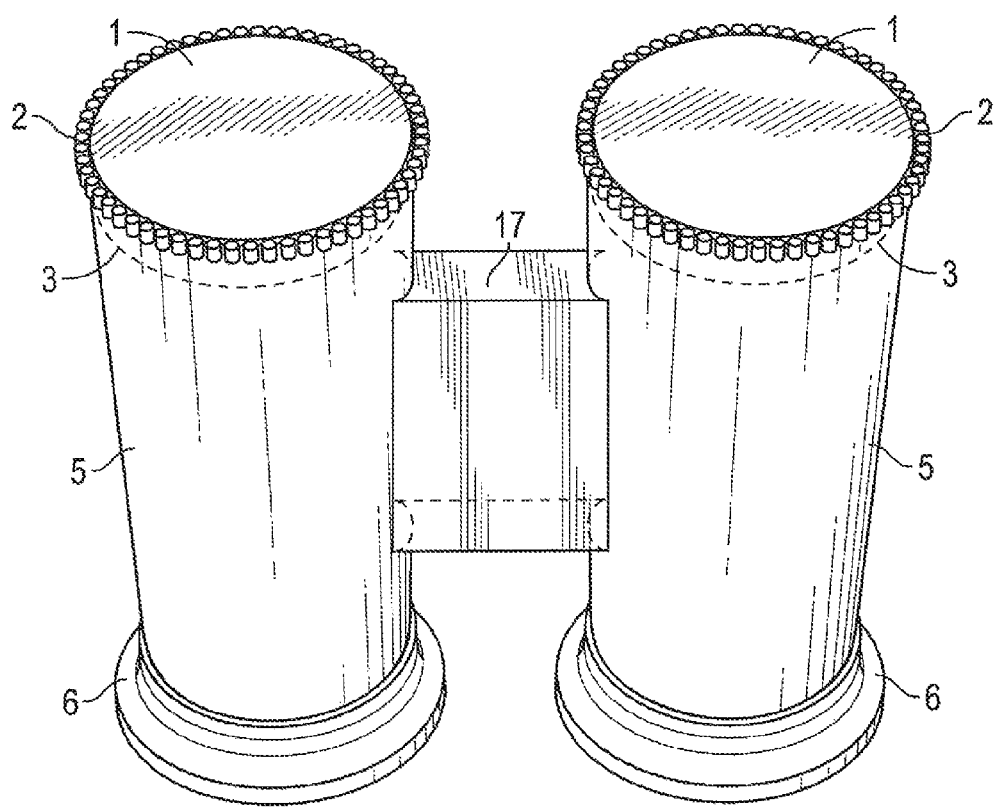

FIG. 8 illustrates the elevated position of the insulin ampule (11) while the bottom of the ampule rests on the inside thick rim of the insert device (7). It also illustrates the domed empty space inside the cap liner (4), FIG. 9 illustrates the two individual cylindrical containers shown in FIG. 1 joined as a single unit.

DETAILED DESCRIPTION OF CONTAINER ASSEMBLY

Referring to one embodiment of the container assembly of this invention as shown in FIG. 1, a cylindrical body comprises the outer casing of the container (5) with a cap (1) having nibs on the cap edge (2) and an anti-toppler ring (6) that stabilizes the cylindrical container so that it would not fall or roll and the notch on the anti-toppler ring (18) prevents the container assembly from rolling in the event it falls.

An inset device (7) as shown in FIG. 2 slips into the cylindrical container (5). The insert device (7) has a thin wall on one end (8) and a thick wall on the opposite end (9). It defines which insulin ampule the container will carry. The insert device (7) is removable, interchangeable, washable and reversible.

When the thin-walled end (8) of the insert device (7) is slipped into the cylindrical container (5) as illustrated in FIG. 3, it adapts the container assembly to accommodate a Lantus® size insulin ampule (10).

When the thick-walled end (9) of the insert device (7) is slipped into the cylindrical container (5) as illustrated in FIG. 4, it adapts the container assembly to accommodate a Novolog®, Humalog® or a Humulin® size insulin ampule (11).

When the thin walled end (8) of the insert device (7) is slipped into the cylinder body (5) first, as illustrated in FIG. 5, it exposes the thick walled end (9) of the insert device (7) to hold the taller Lantus® ampule (10) snuggly in a fixed upright position.

When the thick-walled end (9) of the insert device (7) is slipped into the cylindrical container (5) as illustrated in FIG. 6, it exposes the thin-walled end (8) of the insert device (7) to hold any of the shorter Novolog®, Humalog® or Humulin® insulin ampules (11) snuggly in a fixed upright and elevated position that insures the top of the insulin ampule (14) is at the same level as the cylinder (5) top surface (15).

When a Lantus® insulin ampule (10) is snuggly held by the thick-walled end (9) of the insert device (7) as illustrated in FIG. 7. This stabilizes the ampule in an upright position and leaves the ampule top (14) at the same level as the cylinder top surface (15).

When a Novolog®, Humalog®, or Humulin® insulin ampule (11) is elevated from the bottom of the cylindrical container (5), the insulin ampule rests on the inside thicker rim of the insert device (7) as illustrated in FIG. 8. The inner wall of the thin end (8) of the insert device (7) stabilizes any of the ampules in position and leaves the tops (14) at the same level as the cylinder top surface (15).

When the need to transport more than one insulin ampule arises, the container assembly illustrated in FIG. 1 is attached to a second unit by using a ⅜" thick bridge (17) as illustrated in FIG. 9. This double container assembly accommodates two compactly fitted single units into a double travel size unit. Furthermore, a third unit can be attached for storing an additional ampule for longer travels.

The Cap of the Container Assembly (1):

This is illustrated as a snap-on cap in FIG. 1 (1). The cap (1) top surface is smooth for labeling the container content. The outer edge of the cap is ribbed with ¼" long vertical nibs (2) all around the circumference to allow for easier un-capping of the container. The cap top and nibs are of hard plastic while the cap liner (3) is tapered inward and constructed from soft plastic to ensure a tight seal with the container top surface (15). Furthermore, the cap liner (3) contains an empty domed space ¼" deep inside the cap as illustrated in Figures 1and 8 (4). The purpose of this design is to allow the top of the insulin ampule (14) to sit level with the top surface (15) of the cylindrical container (5). In addition to the snap-on cap design (1), the cap can be constructed with a screw cap design, a child-proof screw cap design, or a snap-on attached design. The cap selection is by preference. When the patient is not handicapped, a regular screw cap design suffices, but where children are involved, a child-proof, tamper resistant cap might be preferred.

Cylindrical Container (5) of the Container Assembly (5):

Referring to FIG. 1, the body of the container assembly consists of a tubular hollow cylinder (5) with a solid flat bottom (12) and an open top (15). The cylindrical container 5) is made of a clear see-through plastic 3/16" thick with graduated markings on the vertical side that allows the patient to determine the volume of insulin remaining in the enclosed insulin ampule. The total outside height of the cylinder from top (15) to bottom is 2⅝" while the inside depth from the top (15) to the bottom is 2½". The flat bottom (12) of the cylindrical container (5) is ⅛" thick. The inside diameter of the cylindrical container (5) is F. It is understood that these measurements pertain to the art when the cylindrical container (5) is used to hold insulin ampules. These measurements could easily vary with other uses of the technology. In addition to carrying insulin ampules as illustrated in FIGS. 4, 5, 6, 7, and 8, the container assembly can carry medicines, liquid or solid, depending upon the type of cap (1) chosen and the exclusion of the insert device (7). The container assembly can be used for taller and wider bottles of liquid or solid pharmaceutical medicines or cosmetic products.

The Insert Device as Illustrated in FIG. 2:

The specialized insert device (7) can be made out of soft non-slippery plastic material that helps maintain the insulin ampules (10, 11) firmly in position inside the container cylindrical container (5). It can also be made of clear acrylic with very close tolerances. The insert device (7) has a wide opening on one end (8) that is ⅞" inside diameter, with a 1/16" "thick wall and is 1" long. On the opposite end, the insert device (7) has a narrower opening (9) that is ¾" inside diameter with ⅛" thick wall and is ⅜" long. The insert device (7) has a total length of 1⅜".

When the insert device (7) is slipped into the container cylindrical container (5) until it touches the bottom (12) as illustrated in FIG. 5 and FIG. 6, its alignment within the cylinder container determines which insulin ampule will fit in the container assembly (5). When the insert device (7) wide open end (8) is placed down into the cylindrical container (5) as illustrated in FIG. 5, then the container accommodates the Lantus® insulin ampule (10) as illustrated in FIG. 7. On the other hand, when the insert device (7) narrower end (9) is placed into the cylindrical container (5) as illustrated in FIG. 6, then the container cylinder (5) accommodates any of the Novolog®, Humalog®, or Humulin® insulin ampules (11).

The difference between the inside diameters of the insert device (7) openings (8 and 9) are determined by the difference in the outside diameters and heights of the various insulin ampules marketed. The inside diameter of the wide opening (8) is ⅞" and it's depth is 1" and accommodates the Novolog® insulin, the Humalog® insulin, and the Humulin® insulin ampules (11). The inside diameter of the narrower opening (9) is ¾" and accommodates the Lantus® insulin ampule (10). When the insert device (7) is resting firmly on the bottom of the cylindrical container (5) as illustrated in FIG. 7 and FIG. 8, the different insulin ampules positioned inside their respective inserts will have their tops (14) level with the container top surface (15). Furthermore, the diameter difference between the two ends (8 and 9) of the insert device (7) allows the Lantus® taller and thinner insulin ampule (10) to reach the bottom (12) of the cylindrical container (5) but restricts the shorter and wider insulin ampules of Novolog®, Humalog® and Humulin® (11) from reaching the bottom of the container cylinder (5) as illustrated in FIG. 8.

Anti-Toppler Ring (6):

A detachable anti-toppler ring (6) is illustrated in FIGS. 1-9. The anti-toppler ring fits on the outside of the cylindrical container (5) and sits snug to the floor in line with the bottom of the container assembly to stabilize its vertical position. The anti-toppler rings (6) as illustrated in FIG. 3 and FIG. 4 are detached from the cylindrical containers (5). The anti-toppler ring is ⅝" high with an internal diameter of 1⅜" and an external diameter at its widest of 1¾". When the anti-toppler rings (6) as illustrated in FIGS. 5-9 are in position at the bottom of the cylindrical container, they form an integral part of the container assembly. The anti-toppler rings are notched on one side (18) to prevent the assembly from rolling off a table top or other flat surface in the event the container assembly falls. It is preferred that the anti-toppler ring (6) be composed of semi-soft clear plastic. On the other hand, if the anti-toppler ring is manufactured attached to the cylindrical container (5), it will have the same material specifications as the cylindrical container (5) itself.

Constructing a Multiple Container Assembly as Illustrated in FIG. 9:

When there is a need to transport more than one insulin ampule at a time, a multiple container assembly design is illustrated in FIG. 9. This design illustrates the construction of a double container assembly formed by the addition of a bridge (17) that joins two independent containers similar to that illustrated in FIG. 1. into a single unit that is simple to pack and carry. The bridge can be constructed from ⅜" thick acrylic and bonded to the side of the cylindrical container (5) to form the double container unit illustrated in FIG. 9. The combined units can easily be produced by combining single container units as illustrated in FIG. 1, into single double-container unit or a single triple-container unit. They can be constructed from various materials such as aluminum, various plastics and clear or pigmented acrylics.

It is anticipated that the container assembly of the invention will primarily be used for holding insulin bottles and the invention has been primarily described herein in that context. However, the invention may be used for any of a number of additional purposes. While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Accordingly, the scope of protection is not limited by the description set out above, and each and every claim below, and its equivalents, are incorporated into the specification as an embodiment of the present invention. Thus, the claims are a further description and are an addition to the preferred embodiments of the present invention.

What is claimed is:

1. A container for an insulin bottle or ampoule having a certain, known size, the container comprising:
    a cylindrical hollow body comprising an outer casing of the container and having a solid flat bottom and an open top;
    a cap having an outer circumference and vertical nibs surrounding the outer circumference;
    an anti-toppler ring having a notch for stabilizing the container or preventing the container from rolling;
    an insert device comprising a thinner wall on one end than on the opposing end and sized so as to fit inside the cylindrical hollow body, and wherein the insert device is removable from the cylindrical hollow body, whereby the insert device is adaptable to supporting insulin bottles of different diameters and heights by removing, inverting and repositioning the insert device inside the cylindrical hollow body;
    a cap liner tapered inward for ensuring a tight seal with the cylindrical hollow body;
    wherein the cap liner contains an empty domed space inside the cap so as to allow the top of any bottle in the container to sit level with a top surface of the cylindrical hollow body.

2. The container of claim 1 further comprising a first bridge for attachment of a second like container for a second bottle.

3. The container of claim 2 further comprising a second bridge for attachment of a third like container for a third bottle.

4. The container of claim 1 wherein the cap has a smooth top surface.

5. The container of claim 1 wherein the cap has a screw cap design for fitting on the cylindrical hollow body.

6. The container of claim 1 wherein the container is comprised of plastic.

7. The container of claim 1 wherein the insert device is comprised of a soft non-slippery plastic material or acrylic formed to fit the cylindrical hollow body allowing no significant slippage between an outer surface of the insert device and the inner surface of the cylindrical hollow body.

8. The container of claim 1 wherein the insert device contacts the bottom of the cylindrical hollow body upon insertion into the cylindrical hollow body to provide height adjustment to accommodate different sized bottles or ampoules so as to result in the top of any ampoule positioned inside the container being level with the top surface of the cylinder.

9. The container of claim 1 wherein the anti-toppler ring is comprised of the same material as the cylindrical hollow body.

10. The container of claim 1 wherein the anti-toppler ring is comprised of a semi-soft plastic.

11. The container of claim 1 wherein the container is comprised of anodized aluminum or other metal.

12. The container of claim 1 wherein the container is comprised of materials ranging from clear to colored such the container is clear or colored.

* * * * *